United States Patent
Henning et al.

(10) Patent No.: US 8,706,197 B2
(45) Date of Patent: Apr. 22, 2014

(54) PLANNING METHOD AND PLANNING DEVICE FOR KNEE IMPLANTS

(75) Inventors: Stefan Henning, Markt Schwaben (DE); Monika Hobelsberger, Poing (DE); Jörg Hächler, Glunn (DE); Michal Slomczykowski, Harrogate (GB)

(73) Assignee: Brainlab AG, Feldkirchen (DE)

( * ) Notice: Subject to any disclaimer, the term of this patent is extended or adjusted under 35 U.S.C. 154(b) by 3291 days.

(21) Appl. No.: 11/115,965

(22) Filed: Apr. 27, 2005

(65) Prior Publication Data

US 2005/0251065 A1    Nov. 10, 2005

Related U.S. Application Data

(60) Provisional application No. 60/579,430, filed on Jun. 14, 2004.

(30) Foreign Application Priority Data

Apr. 27, 2004  (EP) ..................................... 04009937

(51) Int. Cl.
  *A61B 5/05*    (2006.01)
(52) U.S. Cl.
  USPC ............ 600/427; 600/595; 600/424; 600/426
(58) Field of Classification Search
  USPC .................................. 600/595, 424, 426, 427
  See application file for complete search history.

(56) References Cited

U.S. PATENT DOCUMENTS

| | | | |
|---|---|---|---|
| 6,450,978 B1 | 9/2002 | Brosseau et al. | |
| 6,470,207 B1 * | 10/2002 | Simon et al. | 600/426 |
| 6,711,432 B1 * | 3/2004 | Weiss et al. | 600/427 |
| 6,990,220 B2 * | 1/2006 | Ellis et al. | 382/128 |
| 7,167,738 B2 * | 1/2007 | Schweikard et al. | 600/407 |
| 2002/0198451 A1 | 12/2002 | Carson | |
| 2003/0069591 A1 * | 4/2003 | Carson et al. | 606/130 |
| 2003/0176783 A1 * | 9/2003 | Hu | 600/429 |

FOREIGN PATENT DOCUMENTS

| | | |
|---|---|---|
| DE | 100 31 887 | 1/2002 |
| WO | 2004/017836 | 3/2004 |
| WO | 2004/032780 | 4/2004 |

* cited by examiner

*Primary Examiner* — Long V. Le
*Assistant Examiner* — Nicholas Evoy
(74) *Attorney, Agent, or Firm* — Tucker Ellis LLP

(57) ABSTRACT

A planning method and device for knee implants, wherein spatial data on the configuration of a patient's genicular anatomy, in particular of at least a part of the femur and/or the patella and/or the tibia, are captured in order to be inputted into a computer-assisted planning station; the movement of the parts of the genicular anatomy is recorded using a tracking and/or motion capturing method; the captured anatomical and movement data are made available to the computer-assisted planning station; a part of the patient's genicular anatomy is virtually replaced in the planning station by a sample implant and movements of the knee together with the sample implant are simulated; contact and impingement between the non-replaced parts of the genicular anatomy and the implant during the virtual movement is ascertained according to its magnitude; and wherein an adjustment of the positioning, shape or orientation of the implant or of a number of these parameters is determined until the contact and impingement become non-critical and the adjustment thus determined is defined as a suitable adjustment.

19 Claims, 3 Drawing Sheets

PLANNING METHOD AND PLANNING DEVICE FOR KNEE IMPLANTS

RELATED APPLICATION DATA

This application claims priority of U.S. Provisional Application No. 60/579,430 filed Jun. 14, 2004, which is hereby incorporated herein by reference in its entirety.

FIELD OF THE INVENTION

The invention relates to a planning method and device for knee implants.

BACKGROUND OF THE INVENTION

When positioning knee implants, an implant should be attached to the remaining bone in such a way that excessively high strains or strains on one side which can lead to a sensation of pain do not arise later, even during movement. In particular, the patella should be correctly positioned in order to be able to optimally configure its course when the implant is inserted.

In order to take these ancillary conditions into account when planning the implant, a common practice is to perform so-called patella tracking in a very basic embodiment. When "tracking" or "motion capturing" is mentioned in the present text, this then means, in very general terms, tracking the movement of a body with the aid of movement detection means. Thus, a body, or active emitters or passive reflectors attached to the body, can be tracked in order to be able to detect their location at a particular point in time (pre-/intra-/post-operative) and/or their trajectory and thus also the location or trajectory of the body. In particular, passive marker reflectors, which reflect infrared light, can be detected by two infrared light cameras, whereby spatial locations and/or spatial movements of the body can be determined by stereoscopic observation.

In conventional movement detection for the patella as noted above, reference arrays (arrays of, for example, three of the markers mentioned above) are attached to the patella and to the femur and possibly also the tibia, all three bones are registered, and a single point or just a few points on the patella are tracked in order to detect their trajectory relative to the femur.

The disadvantage of these known methods is simply their low yield of information on the relative movement and contact of individual parts of the joint which may be later expected. Point-by-point tracking or motion capturing for individual points on the patella is insufficient for a realistic simulation of the end conditions and therefore also insufficient for optimum planning.

SUMMARY OF THE INVENTION

The present invention provides a planning method and device for knee implants which overcome one or more of the aforesaid disadvantages of the prior art. In particular, the method and system enable optimum planning and thus ensure favorable conditions, also with regard to the position and trajectory of the patella, after the implant has been positioned.

More particularly, a planning method and device for a knee implant procedure according to the invention involve inputting into a computer-assisted planning station spatial data and/or surface contour data on the configuration of a patient's genicular anatomy; capturing anatomical and movement data of relatively moving individual parts of the genicular anatomy using a tracking and/or motion capturing method and supplying the captured anatomical and movement data to the computer-assisted planning station; using the captured anatomical and movement data to display on a display the movement of the individual parts with respect to each other; using the computer-assisted planning station to virtually replace at least a portion of at least one of the individual parts of the patient's genicular anatomy with a virtual implant and to simulate relative movement of the part with the virtual implant and other parts of the genicular anatomy; and using the computer-assisted planning station to determine the intensity of virtual contact or impingement between the implant and another part or between the implant and an implant in another part, and to display the intensity of contact or impingement.

The planning method and device may further involve virtually adjusting the position, shape and/or orientation of the implant or implants to obtained a planned position, shape and/or orientation of the implant or implants that provide an acceptable degree of the contact or impingement. The adjustment may be performed by the user on the basis of the captured contact or impingement data. The contact or impingement may be regarded as acceptable if it indicates substantially symmetrical contact between the parts of the genicular anatomy and/or an avoidance of the patella alta or the patella bacha. The adjustment may be automatically performed using the computer-assisted planning system. The computer-assisted planning system may output data on at least one possible adjustment that can be confirmed or selected by user inputs.

The planning method may further comprise the step of performing knee implant procedure using the planned position, shape and/or orientation of the implant or implants to position the implant or implants in relation to the parts of the patient's genicular anatomy.

Further in accordance with the invention, the parts of the patient's genicular anatomy may be one or more of the femur, patella and tibia of the patient. The captured anatomical and movement data may be recorded and then virtually displayed. The spatial data and/or surface contour data on the configuration of the patient's genicular anatomy may be captured by surface scanning using a scanning instrument that is tracked by a tracking system. The scanning instrument may include a navigated pointer of a surgical navigation system. The spatial data and/or surface contour data on the configuration of the patient's genicular anatomy may be captured by surface scanning with the aid of a tomographic imaging method, such as a CT scanning method.

The captured contact or impingement data on the parts of the genicular anatomy and/or on the implants may be displayed in an image output, wherein image output includes one or more of: the surface of the patella, the surface of the patella sample implant, the distal femur and/or tubercula articulare (condyles), the femur implant, the proximal tibia, the tibia implant and insert/inlet, cross-sectional views through a surface or volume representation of the points cited above, and virtually displayed ligaments or ligament attachment points.

The captured contact or impingement data may be displayed in monotone, monotone with different shadings, or in different colors, depending on the intensity of the contact and/or impingement.

The captured contact or impingement data on the parts of the genicular anatomy and/or on the implants may be displayed as a textual/numerical output or as an additional textual/numerical output in an image output.

The planning method may further comprise the step of virtually adjusting the position, shape and/or orientation of the implant or implants to obtained a planned position, shape and/or orientation of the implant or implants that provide an acceptable degree of the contact or impingement; and wherein the change in the kinematics and/or axis of the leg is determined and optionally taken into account in the adjustment.

BRIEF DESCRIPTION OF THE DRAWINGS

In the following, the invention is described in more detail, wherein reference is made to particular embodiments and to the enclosed drawings, which show.

DETAILED DESCRIPTION

Figure 1:
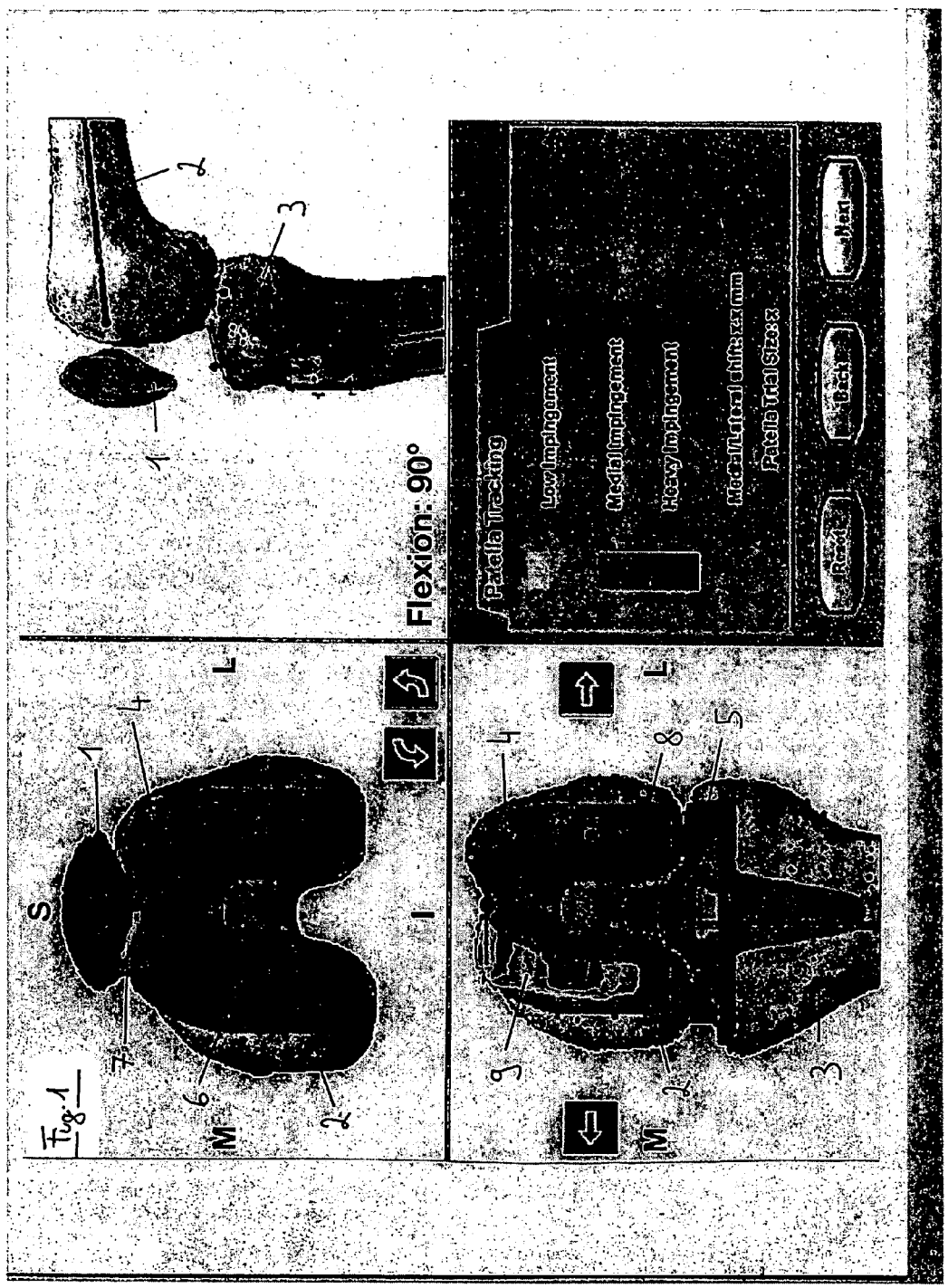
FIG. 1 is a screen shot of a planning system for planning an implant with computer assistance, in which the degree of contact between various parts of the knee and/or implants is shown.

Advantages of the present invention are based on the fact that the patient's genicular anatomy is detected spatially and/or according to its surface contour, such that contact and impingement between the implant and the parts of the genicular anatomy can be detected and simulated far more extensively and with a far higher yield of information. On the basis of these results, a possible problem in a currently proposed implant positioning can then be identified far more precisely than previously, and the positioning can be adjusted until the problem no longer arises.

In other words, the invention is also a part of the patella tracking function of a surgical, computer-assisted planning system. The general idea is also to track the movement of the patella towards the femur, wherein as a post-operative result, the patella or a patella implant should slide on the femur or femur implant in such a way that the patient does not feel any pain at the rear or front part of the patella. This result can be achieved by ensuring that the patella moves anatomically after implantation and no unnatural strains are applied to the patella. This also applies when the sliding surface of the patella is replaced by an implant.

In accordance with a preferred embodiment of the invention, the spatial data of the configuration of the patient's genicular anatomy are captured by surface scanning using a tracked scanning instrument, in particular a navigated pointer of a surgical navigation system. Such an embodiment configures the setting as a whole to be very simple and clear and makes using complicated and expensive apparatus for the surface scanning superfluous. It is particularly advantageous in such scans if the surfaces of the patient's genicular anatomy are scanned or detected which will later contact or move on each other or have contact, i.e. the contact and/or movement surfaces of the parts of the genicular anatomy. It is, however, also possible to not perform the surface scanning until a complete movement of the leg has already been performed and alone the relative movement between the reference systems already attached has been recorded. This procedure is explained even more precisely further below.

Within the framework of the present invention, however, it is not to be completely ruled out that high-precision surface scanning is performed using technical assistance. In accordance with a different embodiment of the present invention, it is thus possible to capture the spatial data of the configuration of the patient's genicular anatomy by surface scanning with the aid of a tomographic imaging method, in particular a CT scan.

The noted scans can be performed pre-operatively or intra-operatively. The movement can also, however, be recorded post-operatively, if for example an implanted reference marker remains in the cited bones of the patient and is for example measured in a magnetic field. If the position of the reference marker with respect to the bone image is known, such as for example by referencing it intra-operatively, then the recorded movement can be compared with the pre-operatively or intra-operatively recorded movements and analyzed.

In one embodiment of the invention, contact or impingement is regarded as non-critical if it indicates substantially symmetrical contacts between the parts of the genicular anatomy and/or an avoidance of the patella alta or the patella bacha.

The positioning, shape or orientation of the implant can be automatically adjusted in accordance with the invention using the computer-assisted planning system. This is not, however, the only possibility. Rather, it is also possible in accordance with the invention to have the computer-assisted planning system output data on at least one possible adjustment, wherein the suitable adjustment can then be confirmed or selected by user inputs. A third possibility is then an adjustment by the user on the basis of the captured contact or impingement data.

Individual parts or a number of portions of the displayed parts can be included in the image output. Widely different methods of display are conceivable here; the captured contact or impingement data can for example be displayed in monotone, monotone with different shadings, or different colors, depending on the intensity of the contact and/or impingement. The contact or impingement data and/or the contact data should be indicated in such a way that they are easy to differentiate. Furthermore, it is possible in accordance with the invention to display the captured contact or impingement data on the parts of the genicular anatomy and/or on the implants as a textual/numerical output or as an additional textual/numerical output in an image output. A textual/numerical output alone is of course also conceivable in principle.

The method in accordance with the invention is also particularly suitable in cases in which ligaments are corrected. In particular in cases in which such a ligament correction has a significant effect on the movement of the knee as a whole or on the trajectory of the patella in particular, the change in the movement of the patella after the length of a knee ligament has been corrected can be determined and optionally taken into account in the adjustment.

Initially, in an exemplary planning method according to the present invention, the movement of the patella in the original state of the knee joint is recorded, when the knee is bent and stretched. This can be done pre-operatively and/or intra-operatively, wherein reference marker arrays are attached to the patella and to the joint ends of the femur and the tibia and tracked using for example a camera-assisted or magnetic tracking system. Before or after the "motion capturing", the surfaces of the patella, the femur and the tibia— in particular the patella and the femur—which come into contact with each other or move on each other when the knee moves are detected according to their outer shape or configuration. This can for example be achieved by traversing the surfaces with the tip of a scanning instruments which is likewise tracked, such that the outer contour is stored in terms of area as a data set in the planning system. The planning system then knows the natural course of movement between the patella and the remaining parts of the joint, and it knows the configuration of the surfaces which contact each other and move on each other, in this anatomical state.

The planning system also comprises data for knee implants, in particular data on the shape of such knee implants. If, at the planning station, a part of the genicular anatomy, for example the joint head of the femur, is then replaced by such a knee implant, e.g. by superimposing the planned femur component onto the patella kinematics, the contact or movement surfaces can be calculated on the basis of the resultant contact or impingement and highlighted in an image representation, such that the surgeon receives information on how the position of the implant affects the tension and kinematics of the patella. In other words, the recorded movement of the patella is shown, for example in an implant positioning planning view, in relation to the femur and a planned femur implant position.

This results for example in a representation in accordance with FIG. 1. In FIG. 1 (and in FIG. 2), the reference numeral 1 designates the patella, the reference numeral 2 the femur, and the reference numeral 3 the tibia. In both figures, an angular position of the knee joint is shown top right in a lateral view, and below it in each case an input/output field of the software. The representation top left shows the femur together with the patella and in FIG. 1, bottom left, the femur and the tibia are shown together with the implants. The femur implant can also be shown in the top right image.

The position of the patella 1 over the femur 2 is shown in FIG. 1, top left. An implant 4 is arranged on the femur 2. On the implant 4 and on the patella, different shading indicates where there is a strong contact (impingement) and where there is a weaker contact when the knee is moved together with the positioned implant. As indicated in the legend bottom right, the darker areas exhibit greater contact than the lighter spots; a dark spot on the femur implant is marked by the reference numeral 6, a light spot on the patella is marked by the reference numeral 7.

The representation bottom left gives similar information for the femur implant 4 and the tibia implant 5. In the simulated course of movement, there is little or no contact at the very light spot 9 on the femur implant, while at the relatively dark spot 8 there is greater contact.

The positioning of the implant can then be adjusted virtually on the basis of this information, for example by virtually offsetting it in the anterior or posterior, medial or lateral, or rotational direction. This can be performed automatically by the planning system on the basis of the degree of contact information or "by hand" by user intervention. In the end, an implant position is found in which the contact intensities are within a desired range.

The contact intensity can for example correspond here to a pressure and/or the direction of the pressure on the patella. The intensity can be ascertained for example at points, over an area or relative to a volume.

Figure 2:
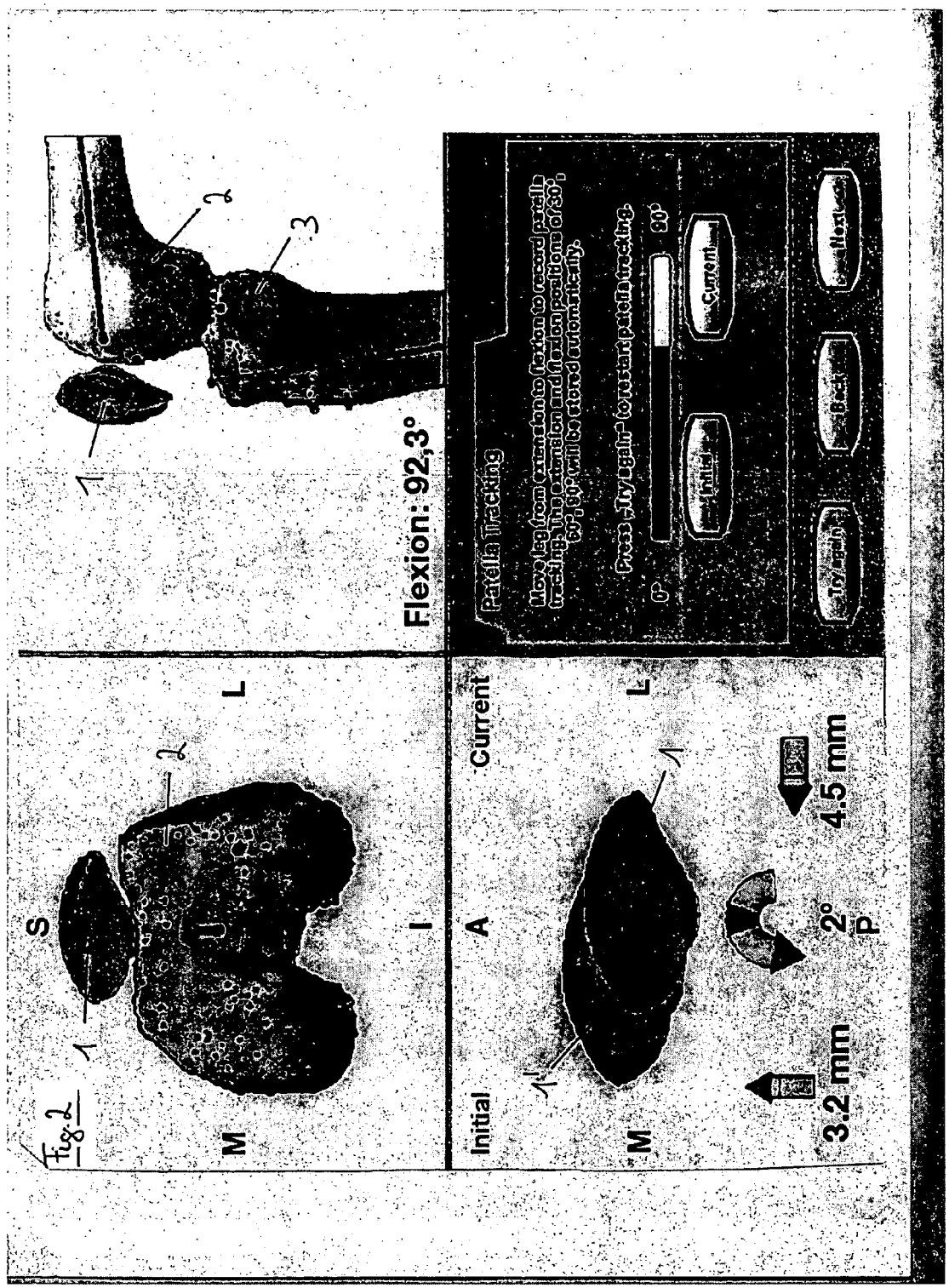
FIG. 2 is a screen shot comprising a representation of the shifting of the patella during knee ligament treatment.

FIG. 2 shows representations for a particular application within the framework of the present invention. For if, during the operation, a change is made to the kinematics and/or axis of the leg, in particular for example lengthening the knee ligaments, it is also to be expected that the trajectory of the patella changes. In order to take these changes in the position of the patella into account, the user of the system in accordance with the invention can record the movement of the parts of the genicular anatomy using the tracking and/or motion capturing method again, after the changes to the ligaments, and make these data available to the planning station. If a course of movement is then simulated again, it can be seen how the position and trajectory of the patella changes, as is shown bottom left in FIG. 2, wherein the reference numeral 1' indicates the original position of the patella and the reference numeral 1 indicates the position of the patella after lengthening the ligament. Below the two representations of the patella, arrows and text also indicate precisely how the position has changed, i.e. for example a shift of 4.5 mm to the left, 3.2 mm upwards and a rotation of 2° anti-clockwise.

In the selection window shown bottom right, the user can then choose whether he wishes to choose the initial trajectory or the current, new trajectory as the basis for positioning the implant. The contact intensity is then shown in turn (see FIG. 1) and the optimum implant position is ascertained.

Once the optimum positioning of the implant has then been established "virtually", the planning method is finished. Using the ascertained planning data, the positioning of a device (template) can be determined, with the aid of which the bones are removed such that the actual implant can be placed and fixed in the optimum position.

The movement can also even be recorded post-operatively, if for example an implanted reference marker remains in the cited bones of the patient and is for example measured in a magnetic field. If the position of the reference marker with respect to the bone image is known, such as for example by referencing it intra-operatively, then the recorded movement can be compared with the pre-operatively or intra-operatively recorded movements and analyzed.

Figure 3:
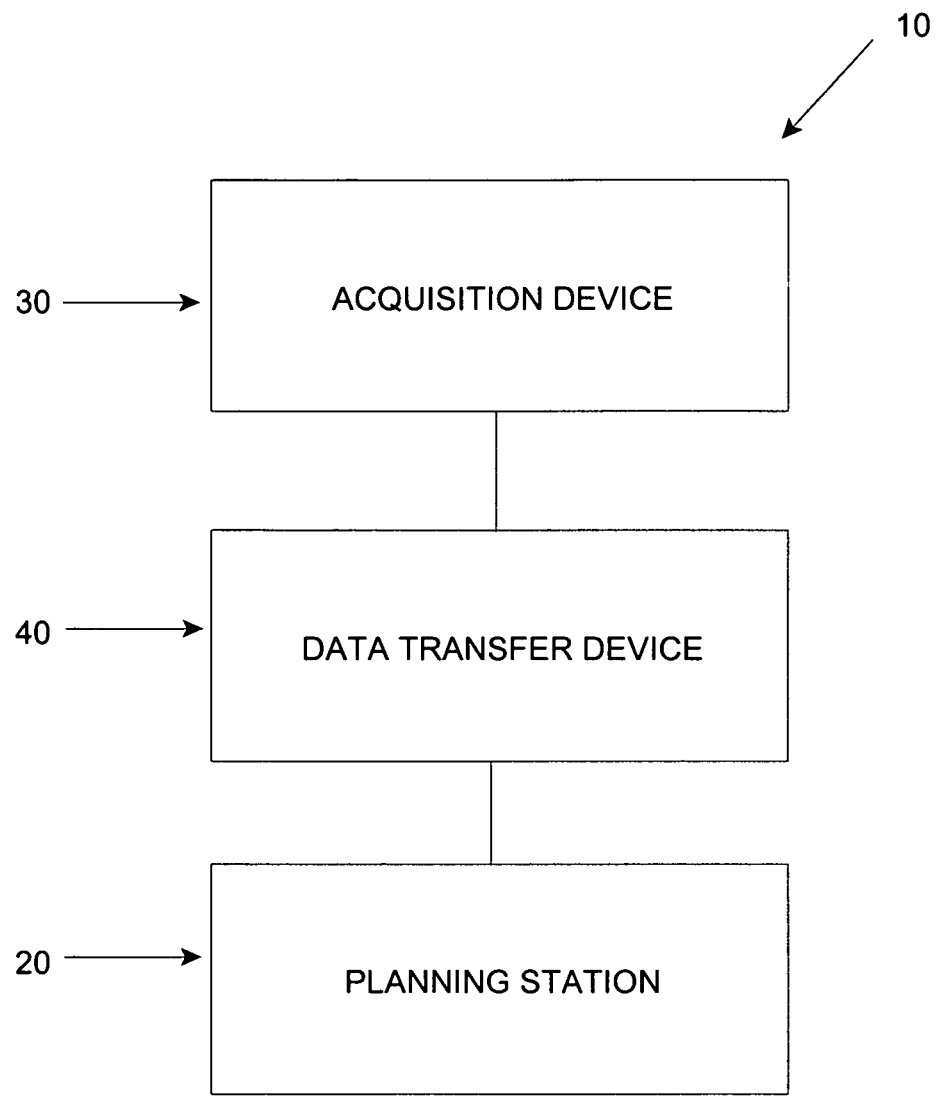
FIG. 3 is a diagrammatic illustration of a device 10 for planning knee implants.

As illustrated in FIG. 3, a device 10 for planning knee implants comprises a computer-assisted planning station 20, into which spatial data and/or surface contour data on the configuration of a patient's genicular anatomy can be inputted; an acquisition device 30 for recording the movement of the parts of the genicular anatomy using a tracking and/or motion capturing method; and a data transfer device 40 for transmitting the anatomical and movement data from the acquisition device to the computer-assisted planning station. The computer-assisted planning station 20 includes a data processing unit operative to use the captured anatomical and movement data to display on a display the movement of the individual parts with respect to each other, to virtually replace at least a portion of at least one of the individual parts of the patient's genicular anatomy with a virtual implant and to simulate relative movement of the part with the virtual implant and other parts of the genicular anatomy, and to determine the intensity of virtual contact or impingement between the implant and another part or between the implant and an implant in another part, and to display the intensity of contact or impingement.

EP 04009937.6, a copy of which is included herewith, is hereby incorporated by reference in its entirety.

What is claimed is:

1. A planning method for a knee implant procedure comprising the steps of:
 capturing at least one of spatial data and/or surface contour data corresponding to a configuration of a patient's genicular anatomy;
 capturing movement data of individual parts of the genicular anatomy moving relative to each other;
 using the captured movement data and the spatial data and/or surface contour data corresponding to the configuration of the patient's genicular anatomy to display on a display device the movement of the individual parts with respect to each other;
 virtually replacing, with computer assistance, at least a portion of at least one of the individual parts of the patient's genicular anatomy with a virtual implant and simulating relative movement of the part with the virtual implant and other parts of the patient's genicular anatomy;

determining, with computer assistance, the intensity of virtual contact or virtual impingement between the implant and another part or between the implant and an implant in another part; and outputting the intensity of virtual contact or virtual impingement.

2. A planning method as set forth in claim 1, further comprising the step of virtually adjusting the position, shape and/or orientation of the implant or implants to obtain a planned position, shape and /or orientation of the implant or implants that provide an acceptable degree of the contact or impingement.

3. A planning method as set forth in claim 2, wherein the adjustment is performed by the user on the basis of the captured contact or impingement data.

4. A planning method as set forth in claim 2, wherein the contact or impingement is regarded as acceptable if it indicates substantially symmetrical contact between the parts of the genicular anatomy and/or an avoidance of the patella alta or the patella bacha.

5. A planning method as set forth in claim 2, wherein the adjustment is automatically performed.

6. A planning method as set forth in claim 2, further comprising outputting data on at least one possible adjustment that can be confirmed or selected by user inputs.

7. A planning method as set forth in claim 2, further comprising the step of performing knee implant procedure using the planned position, shape and/or orientation of the implant or implants to position the implant or implants in relation to the parts of the patient's genicular anatomy.

8. A planning method as set forth in claim 1, wherein the parts of the patient's genicular anatomy include one or more of the femur, patella and tibia of the patient.

9. A planning method as set forth in claim 1, wherein the captured genicular anatomy and movement data is recorded and then virtually displayed.

10. A planning method as set forth in claim 1, wherein the spatial data and/or surface contour data on the configuration of the patient's genicular anatomy are captured by surface scanning using a scanning instrument that is tracked by a tracking system.

11. A planning method as set forth in claim 10, wherein the scanning instrument includes a navigated pointer of a surgical navigation system.

12. A planning method as set forth in claim 1, wherein the spatial data and/or surface contour data on the configuration of the patient's genicular anatomy are captured by surface scanning with the aid of a tomographic imaging method.

13. A planning method as set forth in claim 12, wherein the tomographic imaging method includes a CT scanning method.

14. A planning method as set forth in claim 1, wherein the captured contact or impingement data on the parts of the genicular anatomy and/or on the implants are displayed in an image output, wherein image output can include one or more of:

the surface of the patella,
the surface of the patella sample implant,
the distal femur and/or tubercula articulare (condyles),
the femur implant,
the proximal tibia,
the tibia implant and insert/inlet,
cross-sectional views through a surface or volume representation of the points cited above, and
virtually displayed ligaments or ligament attachment points.

15. A planning method as set forth in claim 14, wherein the captured contact or impingement data are displayed in monotone, monotone with different shadings, or in different colors, depending on the intensity of the contact and/or impingement.

16. A planning method as set forth in claim 1, wherein the contact or impingement data on the parts of the genicular anatomy and/or on the implants are displayed as a textual/numerical output or as an additional textual/numerical output in an image output.

17. A planning method as set forth in claim 1, further comprising the step of virtually adjusting the position, shape and/or orientation of the implant or implants to obtained a planned position, shape and /or orientation of the implant or implants that provide an acceptable degree of the contact or impingement; and wherein the change in the kinematics and/or axis of the leg is determined and optionally taken into account in the adjustment.

18. A non-transitory computer readable medium comprising computer executable instructions adapted to perform the method according to claim 1.

19. A system for planning knee implants, comprising:
a computer-assisted planning station configured to receive at least one of spatial data and/or surface contour data corresponding to a configuration of a patient's genicular anatomy; and
an acquisition device for recording movement of the parts of the genicular anatomy, said acquisition device communicatively coupled to said planning station
wherein the computer-assisted planning station is configured to
virtually replace at least a portion of at least one of the individual parts of the patient's genicular anatomy with a virtual implant,
simulate relative movement of the part with the virtual implant and other parts of the genicular anatomy,
determine the intensity of virtual contact or virtual impingement between the implant and another part or between the implant and an implant in another part, and
to display the patient's genicular anatomy and movement data along with the intensity of contact or impingement.

* * * * *